(12) United States Patent
Mimoun et al.

(10) Patent No.: US 6,177,400 B1
(45) Date of Patent: Jan. 23, 2001

(54) UNSATURATED KETONES AND THEIR USE IN PERFUMERY

(75) Inventors: Hubert Mimoun, Challex (FR); Wolfgang Klaus Giersch, Bernex (CH)

(73) Assignee: Firmenich SA, Geneva (CH)

( * ) Notice: Under 35 U.S.C. 154(b), the term of this patent shall be extended for 0 days.

(21) Appl. No.: 09/306,797

(22) Filed: May 7, 1999

(30) Foreign Application Priority Data

May 8, 1998 (CH) .................................... 1038/98

(51) Int. Cl.$^7$ .............................. A61K 7/46; C07C 69/02; C07C 49/203; C07D 319/06
(52) U.S. Cl. ................................ 512/24; 512/22; 512/23; 512/25; 560/231; 560/259; 568/377; 568/378; 549/369; 549/430
(58) Field of Search ..................................... 568/338, 343, 568/344, 345, 348, 356, 357, 376, 377, 388, 378; 514/690; 512/22, 23, 24, 25; 549/430, 369; 560/259, 231

(56) References Cited

U.S. PATENT DOCUMENTS

| 2,972,632 | 2/1961 | Bain et al. ........................... 260/587 |
| 3,931,326 | 1/1976 | Kovats et al. .................... 260/586 R |
| 4,190,561 | 2/1980 | Auger et al. ...................... 252/522 R |

FOREIGN PATENT DOCUMENTS 2331546   6/1977  (FR) .

OTHER PUBLICATIONS

Aldrich Catalog, pp. 922 and 1267, 1996.*
Andreev et al., "Production of δ–Damascone, Its Analogs And Their Fragrance", *Hydrolysis and Wood Chem.*, pp. 23–25 (1993).
Thomas et al., "The 'Aldol Condensation' of Citral and Related Reactions", *Helvetica Chimica Acta*, vol. 59, Nr. 237, pp. 2261–2267 (1976).
Andreev V.M. et al., "Preparation and Scent of .Delta.–d-amascone and its Analogs", *Chemical Abstracts*, vol. 119, No. 19, Abstract No. 203029 (Nov. 8, 1993).
U. Steiner et al., "Synthese von 1, 1, 5–Trimethyl–2–oxymethyl–cyclohexen–4", *Helvetic Chimica Acta*, vol. 34, pp. 1176–1183 (1951).
Jiang et al., "Carbon–13 NMR Study on the Molecular Structure", *Chemical Abstracts*, vol. 114, No. 3, abstract No. 024251 (Jan. 21, 1991).
Jiang et al., "Carbon–13 NMR Study on the Molecular Structure", *Chinese Journal of Magnetic Resonance*, vol. 7, No. 2, pp. 219–222 (1990).
Érman et al. "Synthesis of Alpha–damascone and 1–(2,6, 6–trimethyl–2–tetrahydropyranyl)–2–alken–1–ones", *Journal of Organic Chimistry of the USSR*, vol. 25, No. 12.2, pp. 2294–2301 (1989).
L. I. Kasumov et al., Study of the Condensation of Diene Hydrocarbons with Mesityl Oxide, *Chemical Abstracts*, vol. 086, No. 11, Abstract No. 071994 (Mar. 14, 1977).

* cited by examiner

Primary Examiner—Sreeni Padmanabhan
(74) Attorney, Agent, or Firm—Pennie & Edmonds LLP

(57) ABSTRACT

The compounds according to the general formula

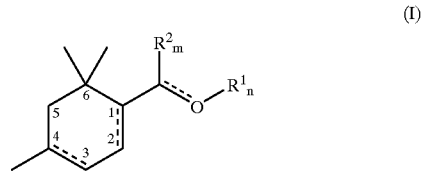

(I)

in which formula the dotted lines indicate a single or a double bond, n and m are 0 or 1, $R^1$ is hydrogen or an acyl group —C(O)$R^3$, $R^3$ being a linear or branched alkyl or alkylene group from $C_1$ to $C_8$, the oxygen atom being bound to the adjacent α-carbon atom by a double bond in the case where n is 0 and by a single bond in the case where n is 1, $R^2$ is hydrogen or a linear or branched alkyl, alkenyl or alkoxy group from $C_1$ to $C_8$, or $R^2$ is an alkenoxy group which is linked to the group $R^1$ to form a 1,3-dioxolane cycle having 5 to 7 ring members, are useful perfuming ingredients. The most preferred compounds according to the invention are those which have a damascone- or damascenone-like structure, with the methyl substituent being in 4-position of the ring instead of the 2-position, as is the case in damascones and damascenones.

18 Claims, No Drawings

UNSATURATED KETONES AND THEIR USE IN PERFUMERY

BRIEF SUMMARY OF THE INVENTION

The present invention relates to the field of perfumery. It relates, more particularly, to compounds derived from the 4,4,6-trimethylcyclohexane skeleton and being represented by the structure according to the general formula (I)

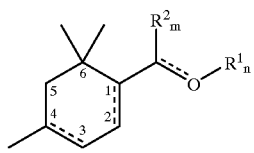

(I)

in which formula the dotted lines indicate a single or a double bond which may optionally be present in the molecule, n and m are 0 or 1, $R^1$ is hydrogen or an acyl group —C(O)$R^3$, $R^3$ being a linear or branched alkyl or alkylene group from $C_1$ to $C_8$, or a substituted or unsubstituted phenyl group, the oxygen atom being bound to the adjacent α-carbon atom by a double bond in the case where n is 0 and by a single bond in the case where n is 1, $R^2$ is hydrogen or a linear or branched alkyl, alkenyl or alkoxy group from $C_1$ to $C_8$, or $R^2$ is an alkenoxy group which is linked to the group $R^1$ to form a 1,3-dioxolane cycle having 5 to 7 ring members.

BACKGROUND OF THE INVENTION

The compounds according to the above formula (I) form a novel class of fragrant molecules the use of which has never been proposed in perfumery. In fact, there exist in this field classes of compounds derived from a cyclohexane ring which carries three methyl substituents, but with a different substitution pattern, as shown in formula (II), in which the dotted lines indicate a double bond which may optionally be present in the $C_6$-ring and R is an organic rest carrying, for example, a keto function

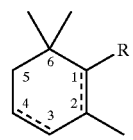

(II)

DETAILED DESCRIPTION OF THE INVENTION

As is clear from a comparison of the two formulae (I) and (II), the compounds known from the prior art are 2,6,6-trimethyl-substituted, which is in contrast to the 4,6,6-trimethyl substitution of the compounds according to the present invention. Well-known examples for the compounds according to formula (II) are damascones and damascenone, in which case R is a —(O)C—CH=CH—$CH_3$ group and the ring carries one double bond in the 1-, 2- or 3-position for damascones, and two double bonds in the 1- and 3-position for damascenone.

To our great surprise, and in spite of the structural ressemblance of the compounds known in the art with the class of molecules according to the present invention and outlined in the above formula (I), we were the first to establish the perfumistic value of these said compounds.

The base molecule which serves as starting product for the synthesis of the class of compounds according to formula (I) is 4,6,6-trimethyl-1,3-cyclohexadiene-1-carbaldehyde, which has for the first time been described by A. F. Thomas et al. in Helv. Chim. Acta 59 (1976), p. 2261–7. As is shown in the scheme (1) below, this compound is then converted into the desired products by the introduction of functional groups, eventually after hydrogenation of one or both of the carbon-carbon double bonds in the $C_6$-ring. As a consequence, the dotted lines in the molecules shown in the scheme below indicate these optionally present double bonds. The reference to the synthesis of the respective compounds in the scheme below is not limiting, refering only to examples for the preparation of the respective class of compounds. The symbols $R^4$–$R^7$ in the scheme (1) will be defined further below, in the paragraphs refering to the respective classes of compounds. The classes of molecules shown in scheme (1) are preferred according to the present invention.

Scheme 1

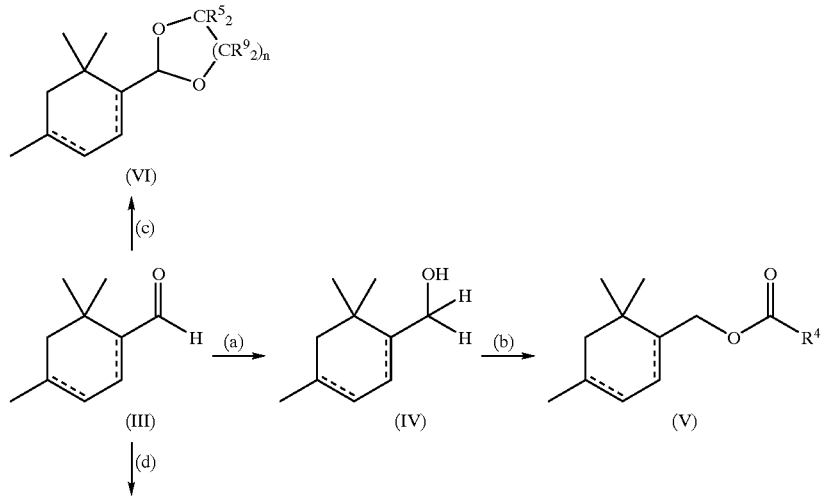

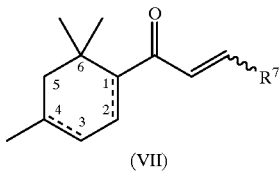

(VII)

a) reduction (e.g. NaBH$_4$, LiAlH$_4$)
b) esterification (e.g. carboxylic acid, anhydride or halide)
c) acetalization (e.g. divalent alcohol)
d) Grignard reagent/hydrolysis; then oxidation [e.g. manganese dioxide, pyridinium dichromate (PDC) or pyridinium chlorochromate (PCC)]

The mentioned carbaldehydes (III) in the above scheme are themselves of perfumistic value. In particular, the 2,2,4-trimethyl-1-cyclohexanecarbaldehyde shows a nice, fresh, aldehyde- and thuyone-like odor with a green connotation reminiscent of Zestover (2,4-dimethyl-3-cyclohexene-1-carbaldehyde; origin: Firmenich SA) and 3,5,5-trimethylhexanal.

The alcohols (IV), obtainable from the above carbaldehydes by reduction of the carbonyl function, show olfactory notes which are different from those of the latter, with the aldehyde note being totally absent. 4,6,6-Trimethyl-1,3-cyclohexadiene-1-methanol has a balsamic-woody note with an incense type connotation being present, somewhat typical of the odor inside a church. The corresponding saturated alcohol, i.e. 2,2,4-trimethyl-1-cyclohexanemethanol, has an odor composed of green and earthy, borneol-camphoraceous-pinanol notes, with a minty connotation being also found.

Another interesting group of compounds, from an olfactory point of view, are the acetals (VI), obtainable from the above-mentioned aldehydes (III) by acetalization. In the above formula (VI), R$^5$ and R$^6$ can be identical or different and are hydrogen or a linear or branched alkyl group from C$_1$ to C$_6$, and n is an integer from 1 to 3. They show woody, fruity and spicy odors, the most interesting compound being 4-methyl-2-(4,6,6-trimethyl-1-cyclohexen-1-yl)-1,3-dioxolan. The odor of this latter is of the woody-camphoraceous type with a strong liquorice undernote, pleasant and appreciated by perfumers.

The esters according to the formula (V) in the above scheme, in which R$^4$ is a linear or branched alkyl group from C$_1$ to C$_8$ or a substituted or unsubstituted phenyl group, have odors of the floral type which are accompanied by undernotes which vary depending on the structure. Amongst the said esters, one preferred compound is (4,4,6-trimethyl-1,3-cyclohexadien-1-yl)methyl isobutyrate which has a complex odor profile, being composed of notes reminiscent of Isopentyrate (1,3-dimethyl-3-butenyl isobutyrate; origin: Firmenich SA), i.e. fruity-floral with a camomile connotation. There are further perceived notes which are typical of damascones, butyrates and carbinols, with a base note of Estragol® (1-allyl-4-methoxybenzene; origin: Givaudan-Roure SA, Vernier, Switzerland). Two other preferred esters are (4,6,6-trimethyl-1-cyclohexen-1-yl)methyl acetate and —butanoate. The acetate has a jasmine note with fruity amylic connotations, whereas the odor of the butanoate is remiscent of orris, with a ionone undernote. Finally, another preferred ester is (2,2,4-trimethyl-1-cyclohexyl)methyl acetate which shows an odor profil reminiscent of Dorysil (4-tert-butyl-1-cyclohexyl acetate; origin: Firmenich SA), i.e. of the fruity-jasmine type, and methylionones, with a woody-hazelnut connotation.

The α,β-unsaturated ketones according to the general formula (VII) in which R$^7$ is a linear or branched alkyl or alkylene group from C$_1$ to C$_4$ are compounds of perfumistic importance. They are structurally related to the well-known damascones or damascenones, but can olfactively be clearly distinguished from these, also due to various pleasant and appreciated undernotes which are not known in combination with the damascone, respectively damascenone-type note which is always found in the molecules according to formula (VII). In general, the damascone-damascenone type odor is accompanied by fruity undernotes. The synthesis and the odor of the compounds according to formula (VII) in which R$^7$ is a methyl group and which has one double bond in position 3 of the cycle is described by V. M. Andreev et al in Hydrolysis and Wood Chem. 1993, p 23–25.

The preferred type of compounds within the group described by the general formula (VII) are the α,β-unsaturated ketones which obey to the general formulae (VIII) and (IX)

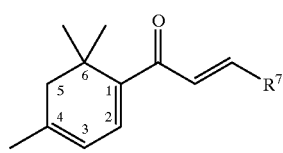

(VIII)

and

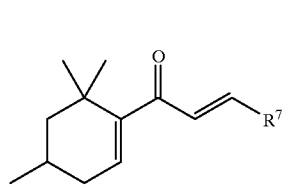

(IX)

wherein R$^7$ is a linear or branched alkyl or alkenyl group from C$_1$ to C$_4$, and which may be in the form of the isomer of the (E) or (Z) configuration, or a mixture of the two.

The compounds of this type are not described in the chemical literature, and the difference between the said compounds and the already mentioned damascones and, respectively damascenones, lies in the position of the methyl substituent at the C$_6$-ring [position 2 for the damascones and damascenones, position 4 for the compounds according to the invention] The damascones and damascenones are highly-appreciated perfuming ingredients, in particular 1-(2,6,6-trimethyl-1,3-cyclohexen-1-yl)-2-buten-1-one, 1-(2,6,6-trimethyl-1,3-cyclohexen-2-yl)-2-buten-1-one, and 1-(2,6,6-trimethyl-1,3-cyclohexadien-1-yl)-2-buten-1-one. This latter compound is found in the oil of the bulgarian rose, and its synthesis, as well as the synthesis of its homologues, is described in the patent U.S. Pat. No. 3,931,326 (assignee: Firmenich SA). The odor of the above-mentioned damascenone forms an own olfactive class in the family of the floral-rose odors, and its olfactive profile is described as being very complex. Olfactive descriptors which are often used are fruity, floral-exotic, reminiscent of the odor of cassis and plums.

However, to our great surprise and in spite of the structural similarity of the compounds (VII) according to the present invention with the damascones and damascenones, we could not find in the chemical literature any mention or even a synthesis for this class of compounds.

We have found that the odor of the compounds (VIII) is quite distinct from that of the damascenones, bringing thus new olfactive notes to the perfumers' palette. In spite of the presence of a typical damascenone-like undernote, the overall olfactive impression is however dominated by other olfactive notes which result in a heretofore unknown, complex odor, wherein spicy, saffron-type, fruity and mirabelle-type odors are quite prononced, however, it is in particular the woody-agarwood type character which is remarkable and dominant.

As an example, there is cited here the compound of formula (VIII) in which R is a methyl group, in particular the isomer of (E)-configuration, or (E)-1-(4,6,6-trimethyl-1,3-cyclohexadien-1-yl)-2-buten-1-one, which is the preferred compound of the invention. The olfactive profile of this molecule is composed of the typical damascenone odor, which is accompanied by a mirabelle accord and, in surplus, a strong woody-saffron note. There are also found a celery type connotation as well as a complex base note, with fruity and floral connotations, reminiscent of jasmine.

The combination of the above-described olfactive characteristics is unique, and the palette of perfuming ingredients which are at the perfumers' disposal is thus enriched by the compounds according to the invention, in particular (E)-1-(4,6,6-trimethyl-1,3-cyclohexadien-1-yl)-2-buten-1-one.

Of course, the use of (E)-1-(4,6,6-trimethyl-1,3-cyclohexadien-1-yl)-2-buten-1-one in perfumery is not restricted to this isomer, it can also be used in form of a mixture with the (Z)-isomer. The proportion of this latter isomer which may be present in in such mixtures depends on the desired olfactive effect, and the person skilled in the art will be perfectly able to choose the desired amount. We have found that mixtures containing at least 90% by weight of the (E) isomer and at most 10% by weight of the (Z)-enatiomer are as advantageous, from an olfactive point of view, the pure (E)-enantiomer.

Like for the compounds of formula (VIII), we could find that the compounds of formula (IX) have odors distinct from those of their known analogs, i.e. the so-called β-damascones. Their odor profile is quite complex, and there are found, besides a typical damascone note which is always present, spicy and resinous notes.

More particulary, the compound according to formula (IX) in which R is a methyl group shows an odor typical of damascone which is accompanied by a strong saffron note. The perfumes could also perceive a floral undernote combined with a spicy connotation of the incense-resinous type, quite original and unknown heretofore.

The compounds according to the present invention can be used in practically every field of modem perfumery. There are cited here the applications in fine perfumery, i.e. in the preparations of perfumes and colognes in which new and original effects can be obtained.

The compounds can also be used in functional perfumery. Non-limiting examples for this type of application include soaps, bath and shower gels, shampoos, deodorants and antiperspirants, air fresheners, liquid and solid detergents for the treatment of textiles and fabric softeners.

In these applications, they can be used alone or in admixture with other perfuming ingredients, solvents or adjuvants of current use in perfumery. The nature and the variety of these coingredients do not require a more detailed description here, which, moreover, would not be exhaustive, and the person skilled in the art will be able to choose the latter through its general knowledge and as a function of the nature of the product to be perfumed and of the desired olfactive effect. These perfuming ingredients belong to chemical classes as varied as alcohols, aldehydes, ketones, esters, ethers, acetates, nitrites, terpene hydrocarbons, sulfur- and nitrogen-containing heterocyclic compounds, as well as essential oils of natural or synthetic origin. A large number of these ingredients is moreover listed in reference textbooks such as the book of S. Arctander, Perfume and Flavor Chemicals, 1969, Montclair, N.J., USA, or its more recent versions, or in other works of similar nature.

The proportions in which the compounds according to the invention can be incorporated in the various products mentioned beforehand vary within a large range of values. These values depend on the nature of the article or products that one desires to perfume and the olfactive effect searched for, as well as on the nature of the coingredients in a given composition when the compound of the invention is used in admixture with perfuming coingredients, solvents or adjuvants of current use in the art.

As an example, and again with reference to the compounds of formula (VII), there can be cited typical concentrations of the order of 0.1 to 1%, or even more, by weight of this compound relative to the weight of the perfuming composition in which it is incorporated. Far lower concentrations than those mentioned can be used when the compound is directly applied for the perfuming of the various consumer products cited beforehand.

The invention will now be described in a more detailed manner in the following examples in which the abbreviations have the usual meaning in the art and the temperatures are given in degrees Celsius.

EXAMPLE 1

Preparation of 4,6,6-trimethyl-1-cyclohexene-1-carbaldehyde

A mixture of 4,6,6-trimethyl-1,3-cyclohexadiene-1-carbaldehyde (141 g, 0.94 mole), ethanol (1 l) and palladium on charcoal (10%, 0.5 g) was hydrogenated by shaking under a $H_2$-atmosphere for 3.5 h. The $H_2$-consumption was 23.5 l. After filtration and concentration of the thus-obtained solution, the residue was distilled at 50°/0.7 hPa, to obtain 125.3 g (87.6%) of the desired product.

Odor: terpenes, metallic. MS: 152($M^+$, 59), 137(42), 123(78), 109(77), 95(48), 81(83), 67(94), 41(100); $^1$H-NMR: 1.0(d, J=6.5 Hz, 3H); 1.17(s, 3H); 1.23(s, 3H); 6.67(dd, $J_1$=2 Hz, $J_2$=6 Hz); 9.35(s, 1H) δ (ppm).

EXAMPLE 2

Preparation of 2,2,4-trimethyl-1-cyclohexanecarbaldehyde 4,6,6-Trimethyl-1,3-cyclohexadiene-1-carbaldehyde (100.0 g, 0.66 mole), 1l of ethyl acetate and 0.3 g of palladium on charcoal (0.3 g) were hydrogenated as described in Example 1, over 3 days. The $H_2$-consumption was 35 l. The mixture was then heated with pyridin chlorochromate to oxidize the amounts of alcohol formed. After filtration and concentration, the product was distilled at 65–73°/18 hPa, to obtain 68.8 g (67%) of the desired product in the form of a mixture of 2 isomers in a ratio of 1:3.

MS: 154(M+, 6), 139(13), 121(11), 110(26), 95(25), 83(66), 69(67), 55(74), 41(100); MS (main isomer): 154 (M+, 7), 139(11), 121(10), 110(27), 95(22), 83(74), 69(93), 41(100); $^1$H-NMR: 0.86(main isomer) and 0.89(two d, J=6.5 Hz), 0.97 and 1.13 (main isomer, two s) and 1.03 and 1.08(two s), 9.8 (main isomer) and 9.92 (two d, J=0.4 Hz) δ (ppm).

EXAMPLE 3

Preparation of 4,6,6-trimethyl-1,3-cyclohexadiene-1-methanol

A solution of 20 g (133 mole) of 4,6,6-trimethyl-1,3-cyclohexadiene-1-carbaldehyde in 100 ml of diethylether was added to a suspension of 1.5 g (39 mmole) of LiAlH$_4$ in diethylether, under stirring and cooling with an ice-bath. After 1 h of reaction time, the mixture was hydrolyzed, the organic layer was separated, washed and dried and concentrated. The crude product was then distilled in vacuo, b.p. 60°/20 hPa, to obtain 11.6 g (56%) of the desired product.

MS: 152(M+, 36), 121(78), 107(100), 91(52), 77(24), 39(17); $^1$H-NMR: 1.02(s, 6H); 1.78(broad s, 3H); 1.98 (broad s, 2H); 4.18(broad s, 2H); 5.63 and 5.81(two m, 2H) δ (ppm).

EXAMPLE 4

Preparation of 4,6,6-trimethyl-1,3-cyclohexene-1-methanol

The procedure described in the above Example 3 was repeated, using 20.7 g (0.136 ml) of 4,6,6-trimethyl-1-cyclohexene-1-carbaldehyde and 1.7 g (0.44 mmole) of LiAlH$_4$ in 200 ml of diethyl ether. Distillation at 70°/0.6 hPa afforded 20.9 g (99%) of pure product.

MS: 154(M+, 17), 139(26), 123(100), 93(67), 81(74), 55(58), 41(95); $^1$H-NMR: 0.93(d, J=7 Hz, 3H); 1.03(s, 3H); 1.09(s, 3H); 4.12(broad s, 2H); 5.64(m, 1H) δ (ppm); $^{13}$C-NMR: 22.3(q); 25.3(d); 28.5(q); 28.8(q); 34.4(s); 34.6 (t); 48.7(t); 63.3(t); 122.9(d); 144.4(s) δ (ppm).

EXAMPLE 5

Preparation of 2,2,4-trimethyl-1-cyclohexanemethanol

The procedure described in the above Example 3 was repeated, using 20 g (0.13 mole) of 2,2,4-trimethyl-1-cyclohexanecarbaldehyde and 1.7 g (45 mmole) of LiAlH$_4$ in 200 ml of diethyl ether. Distillation at 50°/0.5 hPa afforded 18.6 g (92%) of pure product, composed of about 90% of trans and 10% of cis-isomer.

MS: (trans, main isomer): 156(M+, 3), 141(20), 136(17), 123(78), 95(28), 83(100), 69(73), 55(37), 41(30); (cis, minor isomer): 156(M+, 5), 141(9), 138(10), 123(55), 95(27), 83(100), 69(75), 55(40), 41(30); $^1$H-NMR: 0.78(s, 3H); 0.83 (d, J=7, 3H); 0.97(s, 3H); 3.3(dd, J$_1$=10, J$_2$=12, 1H); 3.85 (dd, J$_1$=2.4, J$_2$=10, 1H) δ (ppm); $^{13}$C-NMR: 20.5(q); 22.8 (q); 25.9(t); 28.2(d); 30.9(q); 32.9(q); 35.1(t); 48.9(d); 51.6 (t); 64.5(t) δ (ppm).

EXAMPLE 6

Preparation of (4,4,6-trimethyl-1,3-cyclohexadien-1-yl)methyl isobutyrate

A mixture of 4,4,6-trimethyl-1,3-cyclohexadiene-1-methanol (1.9 g, 12.5 mmole) and pyridine (5 ml) was cooled (ice bath) and stirred, then isobutyryl chloride (1.9 ml, 18 mmol) was added dropwise. After stirring overnight at room temperature, the reaction mixture was poured onto ice, extracted with pentane, washed with HCl (10%), NaHCO$_3$ (5%) and brine.

Distillation at a bath temperature of 80°/0.4 hPa afforded 2.17 g (78%) of pure product.

MS: 222(M+, 12), 134(20), 119(100), 105(20), 91(26), 71(24), 43(53); $^1$H-NMR: 1.02(s, 6H); 1.18(d, J=6.5 Hz, 6H); 1.78(s, 3H); 2.0(s, 2H); 2.57(hept, 1H); 4.6(s, 2H); 5.64(m, 1H); 5.85(d, J=5 Hz) δ (ppm).

EXAMPLE 7

Preparation of (4,6,6-trimethyl-1-cyclohexen-1-yl) methyl acetate

A mixture of 4,6,6-trimethyl-1-cyclohexene-1-methanol (3 g, 19.5 mmole) and acetic anhydride (2.4 g, 24 mmole) was heated to 70° during 3 h, then distilled at a bath temperature of 70°/0.5 hPa, to obtain 3.27 g (86%) of the desired product.

MS: 196(M+, 3), 154(34), 139(32), 121(72), 93(55), 79(42), 43(100); $^1$H-NMR: 0.94(d, J=7 Hz, 3H); 1.2(s, 3H); 1.08(s, 3H); 2.07(s, 3H); 4.55(s, 2H); 5.67(m, 1H) δ (ppm); $^{13}$C-NMR: 21.2(q); 22.2(q); 25.1(d); 28.3(q); 28.6(q); 34.5 (s); 34.6(t); 48.4(t); 65.5(t); 126.9(d); 139.2(s); 170.9(s) δ (ppm).

EXAMPLE 8

Preparation of (4,6,6-trimethyl-1-cyclohexen-1-yl) methyl butyrate

The procedure described in Example 7 was repeated, using 3.7 g (24 mmole) of butyric anhydride. After distillation at a bath temperature of 100°/0.5 hPa, 3.74 g (86%) of pure product were obtained.

MS: 224 (M+, 5), 154(57), 139(62), 121(87), 93(66), 71(61), 43(100); $^1$H-NMR: 0.93(d, J=7 Hz, 3H); 0.94(tr, J=7 Hz, 3H); 1.02(s, 3H); 1.08(s, 3H); 1.67(q, J=7 Hz, 2H); 4.53(s, 2H); 5.66(m, 1H) δ (ppm); $^{13}$C-NMR: 13.7(q); 18.5(t); 22.2(q); 25.1(a); 28.4(q); 28.7(q); 34.5(s); 34.6(t); 36.5(t); 48.5(t); 65.3(t); 126.7(d); 139.3(s); 173.5(s) δ (ppm).

EXAMPLE 9

Preparation of 4-methyl-2-(4,6,6-trimethyl-1-cyclohexen-1-yl)-1,3-dioxolan 4,6,6-Trimethyl-1-cyclohexen-1-carbaldehyde (2 g, 13 mmole), 1,2-propanediol (4 g, 53 mmole) and p-toluenesulfonic acid (50 mg) were refluxed in 20 ml of toluene, with water separation in a Dean-Stark apparatus, during 6 h. The resulting solution was washed with a NaHCO$_3$ solution and the crude product distilled at a bath temperature of 80°/0.5 hPa, to obtain 1.78 g of the desired product in the form of a mixture of isomers.

MS (main peak): 210 (M+, 28), 195(22), 153(100), 113 (26), 87(30), 59(20), 41(15); $^1$H-NMR: 0.93(d, J=6.5 Hz, 3H); 1.1(s, 3H); 1.13(s, 3H); 6.0 and 6.05(two m, 1H) δ (ppm).

EXAMPLE 10

Preparation of 1-(2,2,4-trimethyl-1-cyclohexyl)-2-buten-1-one 2,2,4-Trimethyl-1-cyclohexanecarbaldehyde (11 g, 72 mmole) in ether (100 ml) was added dropwise with stirring to a Grignard compound prepared from Mg (2.3 g) and allylbromide (10 g) in ether and refluxed for 2 h. After cooling, the mixture was hydrolyzed with $NH_4Cl$-solution, then distilled at a bath temperature of 150°/0.5 hPa, to obtain 11.3 g (80%) of the desired product as a 2:1 mixture of 2 isomers.

MS (main isomer): 194 ($M^+$, 0), 163(1), 155(28), 137(76), 111(46), 95(56), 81(72), 69(60), 57(100), 41(97);

MS (minor isomer): 194 ($M^+$, 0), 163(1), 155(25), 137 (76), 111(45), 95(50), 81(67), 69(76), 57(88), 41(100); $^1$H-NMR: 0.82(minor isomer) and 0.83(main isomer) (two d, J=7 Hz, 3H); 0.87& 1.07(minor isomer) two s and 0.93 & 0.97(main isomer) two s; 3.75(minor isomer) and 3.93(main isomer) two m, 1H δ (ppm).

The thus-obtained product (8 g, 40 mmole) was then oxidized in 100 ml of $CH_2Cl_2$ with 16 g of pyridinium chlorochromate at room temperature and overnight. After addition of ether (200 ml), the mixture was filtered and distilled at a bath temperature of 130°/0.4 hPa, to obtain 2.1 g (26%) of the desired product as a mixture of 3 isomers in the ratios of 12:12:15.

Odor: green, aldehyde. MS: 194 ($M^+$, 4), 179(5), 153(7), 125(32), 83(26), 69(100), 55(31), 41(47); 194 ($M^+$, 7), 179(5), 151(9), 125(14), 83(21), 69(100), 55(22), 41(38); 194 ($M^+$, 6), 179(3), 151(6), 125(10), 83(18), 69(100), 55(24), 41(38) (main isomer); $^1$H-NMR (mixture): 0.84 (main) and 0.87(minor) (two d, J=7 Hz, 3H); 0.97 and 0.975 (two s, 6H); 3.31(dtr, $J_1$=6.8, $J_2$=1 Hz, 3H); 5.1(dq, $J_1$=16, $J_2$≈1) and 5.17(dq, $J_1$=10, $J_2$≈1, 1H); 5.82–5.97(m, 1H) δ (ppm).

EXAMPLE 11

Preparation of (4,6,6-trimethyl-1-cyclohexen-1-yl)-2-buten-1-one

This compound was prepared using the procedure described in Example 10, replacing 4,6,6-trimethyl-1-cyclohexene-1-carbaldehyde (10.9 g, 72 mmole) for 2,2,4-trimethyl-1-cyclohexanecarbaldehyde. The desired product was obtained, after distillation at a bath temperature of 130°/0.5 hPa in a yield of 80% in the form of a product having a purity of 70%.

MS: 192 ($M^+$, 27), 177(100), 135(19), 121(23), 81(29), 69(86), 55(18), 41(78); $^1$H-NMR: 0.98(d, J=6.3 Hz, 3H); 1.08(s, 3H); 1.19(m, 1H); 1.30(s, 3H); 1.42(m, 1H); 1.76(m, 1H); 1.88(m, 1H); 1.88(dd, $J_1$=7.3 Hz, $J_2$=1.6 Hz, 3H); 2.27(m, 1H); 6.42(dd, $J_2$=2.4 Hz and 5.6 Hz, 1H); 6.45(dq, $J_1$=14.8 Hz, $J_2$=1.6 Hz, 1H); 6.74(dq,$J_1$=14.8 Hz and 7.3 Hz, 1H) δ (ppm); $^{13}$C-NMR: 18.2(q); 22.1(q); 24.5(d); 28.3(q); 28.4(q); 34.8(s); 34.9(t); 49.1(t); 130.7(d); 137.0(d); 142.5 (d); 146.9(s); 194.6(s) δ (ppm).

EXAMPLE 12

Preparation of 1-(4,6,6-trimethyl-1,3-cyclohexadien-1-yl)-2-buten-1-one 32 g of 4,6,6-trimethyl-1,3-cyclohexadiene-1-carbaldehyde [prepared according to A. F. Thomas et al., Helv. Chim. Acta, 59 (1976), p. 2261–7] in 80 ml of THF were added dropwise to a Grignard compound which had been prepared beforehand from 6 g of magnesium turnings and 32 g of 1-bromo-1-propene in 120 ml of THF. The temperature was maintained at 20° with a water bath during the addition, after which the mixture was heated and kept at reflux over 30 minutes. The reaction mixture was poured into an ice/water ixture and then extracted with ether. The organic phase was washed to neutrality, dried and concentrated. The crude product was then oxidized with 210 g of activated manganese dioxide (see Houben Weyl, Vol. 7, 1, page 178, 1951; E. M. Goldman, Org. Chem., 34, 1979, 1969) in 200 ml of petroleum ether.

After filtration and evaporation of the solvent, 17 g of a product constituted of several compounds and having a boiling point of 42–80°/10 Pa were obtained. The desired (Z)- and (E)-1-(4,6,6-trimethyl-1,3-cyclohexadien-1-yl)-2-buten-1-one were isolated by preparative gas chromatography. The analytical data were as follows:

(Z)-1-(4,6,6-trimethyl-1,3-cyclohexadien-1-yl)-2-buten-1-one

MS: 69(100); 121(59); 41(40); 149(32); 105(27); 190 (26); 91(17); 39(13); 77(11); 79(11); NMR ($CDCl_3$): 1.2 (s, 6H); 1.85 (broad s, 3H); 1.85 (d, J=6,5 Hz, 3H) superposed on 2.05 (m, 2H); 5.7–6.8 (H vinyl, 4H) δ (ppm).

(E)-1-(4,6,6-trimethyl-1,3-cyclohexadiene-1-yl)-2-buten-1-one

MS: 69(100); 121(57); 41(33); 190(27); 105(23); 91(13); 39(13); 175(11); NMR ($CDCl_3$): 1.17 (s, 6H); 1.86 (d, J=5 Hz, 3H); 1.84 (broad s, 3H); 2.05 (broad s, 2H); 5.77 (broad d, J=6 Hz, 1H); 6.38 (d, J=15 Hz, 1H, superposed on signals of 2 other protons) δ (ppm).

EXAMPLE 13

Preparation of a Floral-Green Type Accord

A base type accord was prepared from the following ingredients:

| Ingredients | Parts by weight |
| --- | --- |
| Benzyl acetate | 10 |
| Phenylethyl acetate | 50 |
| 10% Undecylenic aldehyde* | 10 |
| 10% C12 aldehyde | 10 |
| Methyl cinnamate | 5 |
| Citronellol | 200 |
| Eugenol | 10 |
| Geraniol | 150 |
| Iralia ®[1)] total | 40 |
| Linalol | 100 |
| Lorysia ®[2)] | 50 |
| 10% Rose oxide* | 5 |
| Phenethylol | 260 |
| Phenylhexanol | 50 |
| Polysantol ®[3)] | 10 |
| Total | 960 |

*in dipropylene glycol
[1)]methylionones mixture; origin: Firmenich SA, Geneva, Switzerland
[2)]mixture of cis- and trans-4-(1,1-dimethylethyl)-1-cyclohexyl acetate; origin: Firmenich SA, Geneva, Switzerland
[3)]3,3-dimethyl-5-(2',2',3'-trimethyl-3'-cyclopenten-1'-yl)-4-penten-1-ol; origin: Firmenich SA, Geneva, Switzerland When there were added to this base type composition 40 parts by weight of a 10% solution of (E)-1-(4,6,6-trimethyl-1,3-cyclohexadiene-1-yl)-2-buten-1-one in dipropylene glycol, this very floral accord acquired a woody connotation and a fruity-spicy undernote. The perfumers could also perceive, in the floral note of the composition, a touch of carnation which was not present in the base composition.

EXAMPLE 14

Preparation of a Floral-Green, Woody-Fruity Accord

A base type accord of the above mentioned type was prepared from the following ingredients:

| Ingredients | Parts by weight |
| --- | --- |
| Benzyl acetate | 15 |
| Styrallyl acetate | 10 |
| 10% (Z)-3-hexenol acetate* | 25 |
| γ-Decalactone | 2 |
| Dihydroeugenol | 5 |
| Galbex ®[1)] | 5 |
| Habanolide ®[2)]* | 130 |
| Hedione ®[3)] | 150 |
| Iralia ®[4)] | 45 |
| Iso E Super[5)] | 35 |
| Isopentyrate[6)] | 3 |
| Lavandin oil | 15 |
| 10% Liffarome ®[7)]* | 5 |
| (Z)-3-Hexenol salicylate | 120 |
| Scentenal ®[8)] | 10 |
| 10% Trifernal ®[9)]* | 5 |
| γ-Undecalactone | 5 |
| Bergamote base, synthetic[10)] | 100 |
| Lily of the valley base, synthetic[10)] | 175 |
| Wardia ®[11)] | 90 |
| Vert de lilas[12)] | 10 |
| Ylang-ylang | 15 |
| Total | 980 |

*in dipropylene glycol
[1)]galbanum base; origin: Firmenich SA, Geneva, Switzerland
[2)]mixture of 1-oxa-12-cyclohexadecen-1-one and 1-oxa-13-cyclohexadecen-2-one; origin: Firmenich SA, Geneva, Switzerland
[3)]methyl dihydrojasmonate; origin: Firmenich SA, Geneva, Switzerland
[4)]see example 2
[5)]origin: International Flavors & Fragrances, USA
[6)]1,3-dimethyl-3-butenyl isobutyrate; origin: Firmenich SA, Geneva, Switzerland
[7)](Z)-3-hexenyl methyl carbonate; origin: International Flavors & Fragrances, USA
[8)]mixture of 8- and 9-methoxy-tricyclo[5.2.1(2.6)]decane-3(4)-carbaldehyde; origin: Firmenich SA, Geneva, Switzerland
[9)]3-phenylbutanal; origin: Finnenich SA, Geneva, Switzerland
[10)]origin: Firmenich SA, Geneva, Switzerland
[11)]rose type composition; origin: Firmenich SA, Geneva, Switzerland
[12)](2,2-dimethoxyethyl)benzene; origin: Firmenich SA, Geneva, Switzerland When there were added to this floral base-type composition 20 parts by weight of a 10% solution of (E)-1-(4,6,6-trimethyl-1,3-cyclohexadiene-1-yl)-2-buten-1-one in dipropylene glycol, the perfumers could observe that the lactonic aspect of this accord is intensified, resulting in a nice fruity connotation. Likewise, the floral accord and the green notes are rounded off. There could furthermore be remarked a slightly woody connotation and an undernote of the mirabelle type, nice and very fruity, which was typically confered by the above compound according to the invention.

What is claimed is:

1. A method to improve, enhance or modify the odor of a perfume or a perfuming composition, which method comprises adding to said perfume or composition a compound according to the general formula (1):

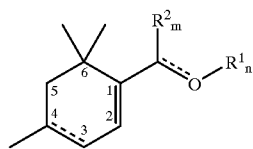

in which formula the dotted lines indicate a single or a double bond, n and m are 0 or 1, $R^1$ is hydrogen or an acyl group —C(O)$R^3$, $R^3$ being a linear or branched alkyl or alkylene group from $C_1$ to $C_8$, or a substituted or unsubstituted phenyl group, the oxygen atom being bound to the adjacent α-carbon atom by a double bond in the case where n is 0 and by a single bond in the case where n is 1, $R^2$ is hydrogen or a linear or branched alkyl, alkenyl, or alkoxy group from $C_1$ to $C_8$, or $R^2$ is an alkenoxy group which is linked to the group $R^1$ to form a 1,3-dioxolane cycle having 5 to 7 ring members, provided that 1-(4,6,6-trimethyl-1-cyclohexen-3-yl)-2-buten-1-one and 4,6,6-trimethyl-1,3,-cyclohexadiene-1-carbaldehyde are excluded.

2. The method according to claim 1, wherein the compound is of the general formula

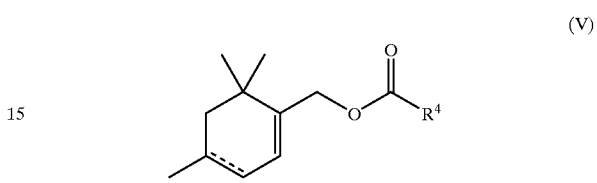

wherein $R^4$ is a linear or branched alkyl group from $C_1$ to $C_8$ or a substituted or unsubstituted phenyl group and the dotted line represents a single or double bond.

3. The method according to claim 1, wherein the compound is of the general formula

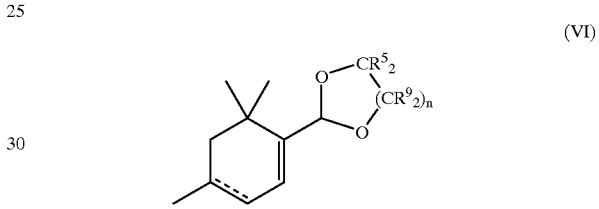

wherein $R^5$ and $R^6$ can be identical or different and are hydrogen or a linear branched alkyl group from $C_1$ to $C_6$ and n is an integer from 1 to 3, and the dotted line indicates a single or double bond.

4. The method according to claim 1, wherein the compound is of general formula

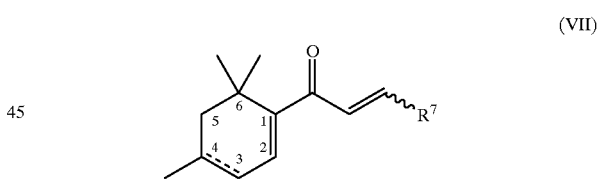

wherein $R^7$ is a linear or branched alkyl or alkylene group from $C_1$ to $C_4$, and the dotted line indicates a single or double bond, provided that 1-(4,6,6-trimethyl-1-cyclohexen-3-yl)-2-buten-1-one is excluded.

5. The method according to claim 1, wherein the compound is of the general formula

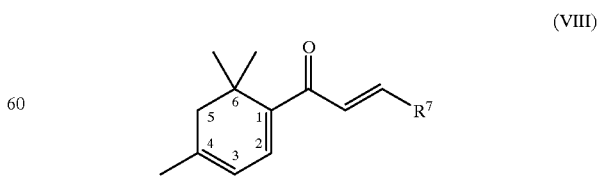

wherein $R^7$ is a saturated or unsaturated, linear or branched hydrocarbon radical from $C_1$ to $C_4$, in the form of an isomer of the configuration (E) or (Z), or a mixture of both.

6. The method according to claim 5, wherein there is used a mixture containing at least 90% by weight of (E)-1-(4,6,6-trimethyl-1,3-cyclohexadien-1-yl)-2-buten-1-one and 10% or less by weight of (Z)-1-(4,6,6-trimethyl-1,3-cyclohexadien-1-yl)-2-buten-1-one.

7. The method according to claim 1, wherein the compound is of the general formula

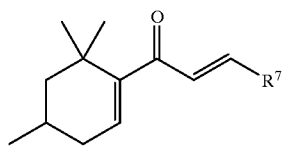

(IX)

in which $R^7$ is a saturated or unsaturated, linear or branched hydrocarbon radical from $C_1$ to $C_4$, in the form of an isomer of the configuration (E) or (Z), or a mixture of both.

8. Perfuming composition or perfumed article, containing as perfuming ingredient a compound according to claim 1.

9. Perfumed article according to claim 8, in the form of a perfume or cologne, a soap, a bath or shower gel, a shampoo or other hair care product, a deodorant or antiperspirant, an air freshener, a cosmetic preparation, a detergent or fabric softener or an all-purpose cleaner.

10. A compound according to the general formula

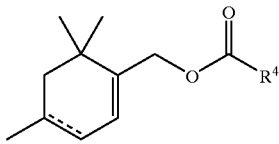

(V)

wherein $R^4$ is a linear or branched alkyl group from $C_1$ to $C_8$ or a substituted or unsubstituted phenyl group, and the dotted line represents a single or double bond.

11. A compound according to the formula

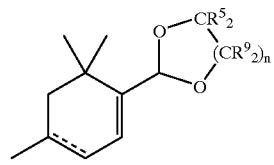

(VI)

wherein $R^5$ and $R^6$ can be identical or different and are hydrogen or a linear or branched alkyl group from $C_1$ to $C_6$ and n is an integer from 1 to 3, and the dotted line indicates a single or double bond.

12. A compound according to the general formula

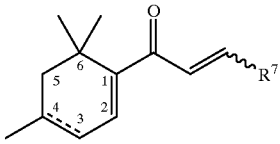

(VII)

wherein $R^7$ is a linear or branched alkyl or alkylene group from $C_1$ to $C_4$, and the dotted line indicates a single or double bond, provided that 1-(4,6,6-trimethyl-1-cyclohexen-3-yl)-2-buten-1-one is excluded.

13. A compound according to the general formula

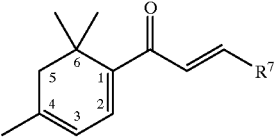

(VIII)

in which $R^7$ is a saturated or unsaturated, linear or branched hydrocarbon radical from $C_1$ to $C_4$, with the proviso that $R^7$ is not methyl, in the form of an isomer of the configuration (E) or (Z), or a mixture of both.

14. (E)-1-(4,6,6-Trimethyl-1,3-cyclohexadien-1-yl)-2-buten-1-one.

15. Mixture containing at least 90% by weight of (E)-1-(4,6,6-trimethyl-1,3-cyclohexadien-1-yl)-2-buten-1-one and 10% or less by weight of (Z)-1-(4,6,6-trimethyl-1,3-cyclohexadien-1-yl)-2-buten-1-one.

16. A compound according to the general formula

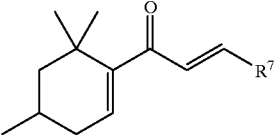

(IX)

in which $R^7$ is a saturated or unsaturated, linear or branched hydrocarbon radical from $C_1$ to $C_4$, in the form of an isomer of the configuration (E) or (Z), or a mixture of both.

17. Perfuming compositions or perfumed articles, containing as a perfuming ingredient a compound according to claim 5.

18. A perfumed article according to claim 17, in the form of a perfume or cologne, a soap, bath or shower gel, a shampoo or other hair care product, a deodorant or antiperspirant, an air freshener, a cosmetic preparation, a detergent or fabric softener, or an all purpose cleaner.

* * * * *

UNITED STATES PATENT AND TRADEMARK OFFICE
CERTIFICATE OF CORRECTION

PATENT NO. : 6,177,400 B1
DATED : January 23, 2001
INVENTOR(S) : Hubert Mimoun et al.

Page 1 of 1

It is certified that error appears in the above-identified patent and that said Letters Patent is hereby corrected as shown below:

Columns 1-2,
Scheme 1, replace formula (VI) with the following:

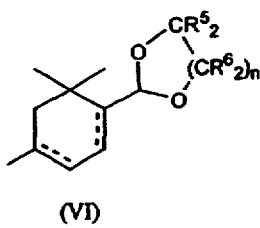

(VI)

Signed and Sealed this

Twenty-seventh day of November, 2001

Attest:

*Nicholas P. Godici*

NICHOLAS P. GODICI
*Attesting Officer*    *Acting Director of the United States Patent and Trademark Office*

UNITED STATES PATENT AND TRADEMARK OFFICE
CERTIFICATE OF CORRECTION

PATENT NO.    : 6,177,400 B1
DATED         : January 23, 2001
INVENTOR(S)   : Hubert Mimoun et al.

It is certified that error appears in the above-identified patent and that said Letters Patent is hereby corrected as shown below:

Column 12,
Lines 26-33, replace the formula with the following:

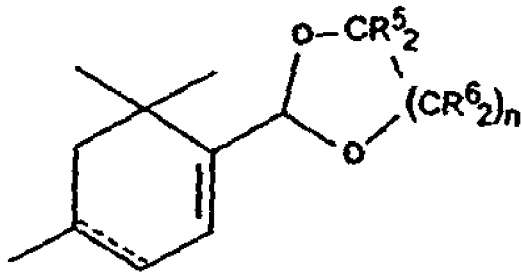

Column 13,
Lines 43-50, replace the formula with the following:

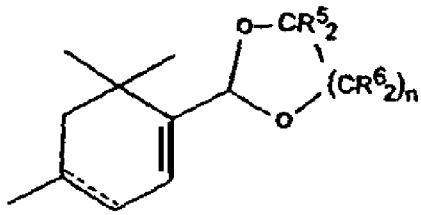

Signed and Sealed this

Twenty-fifth Day of June, 2002

*Attest:*

*Attesting Officer*

JAMES E. ROGAN
*Director of the United States Patent and Trademark Office*